Aug. 27, 1974 L. GRASSO Plant Pat. 3,600
CARNATION PLANT
Filed April 24, 1973
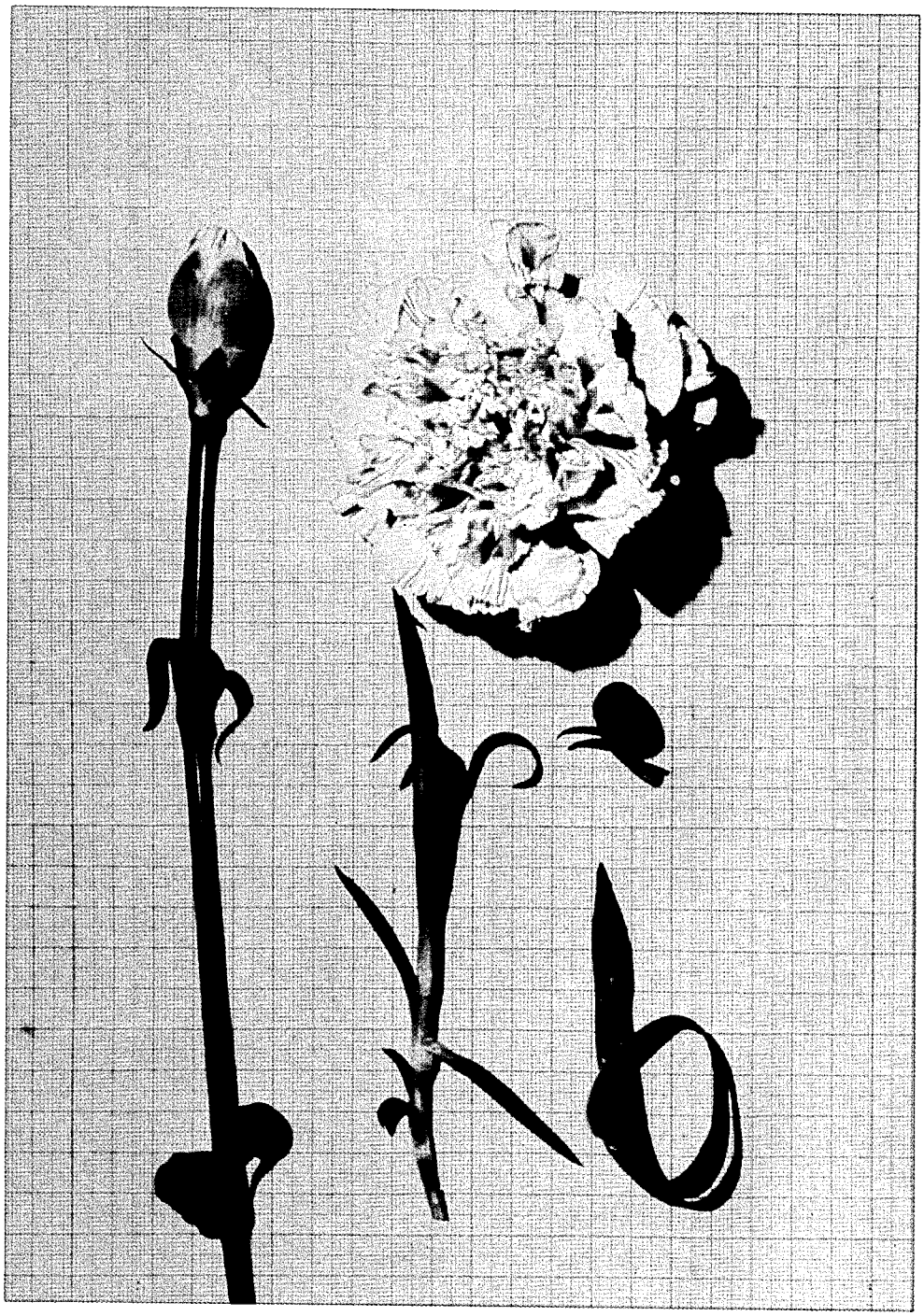

United States Patent Office

Plant Pat. 3,600
Patented Aug. 27, 1974

3,600
CARNATION PLANT

Louis Grasso, Lingostiere, Route de Grenoble,
06 Nice, France

Filed Apr. 24, 1973, Ser. No. 354,147
Claims priority, application France, Apr. 24, 1972, 95
Int. Cl. A01h 5/00
U.S. Cl. Plt.—70 1 Claim The present invention relates to a new and distinct variety of carnation plant which is a sport of the variety "Sylvie" (Sylvia).

The present inventor observed that carnation plants of the variety sold commercially as "Sylvie" had from time to time certain branches whose flowers were different from those common to this variety: the coloration of the corolla was different from the usual color which is almost white finely dappled with rose. The new coloration was basically pale rose shaded and dappled with Rose Clairet at the center of the petals and on the edges of the petals.

This new spontaneous variation of a few flowers on plants of the variety "Sylvie" was of remarkable interest because of this unique combination of colors. However, there were no plants thus characterized but only an occasional flower. Therefore, the present applicant began culture of a new sport based on these occasional flowers, by selecting branches which tended to give flowers of the new color. In this way, it was possible to produce the new and distinct variety of the present invention, which is different from the mutant plant from which it was derived and also from all other varieties of its class.

The new variety thus is characterized by these new flowers, and may be easily reproduced in an infinite number of examples having all the characteristics of the original sport, by asexual reproduction according to methods commonly used in the flower culture industry and particularly by strike rooting slips or cuttings or lateral sheets or other parts of the plant of the present invention.

As a result of having thus asexually reproduced the plant many times, the present inventor has found that the characteristics described below are transmitted from plant to plant with constancy and fidelity and that the plant population thus reproduced is quite homogeneous and stable as to the characteristics described below.

These characteristics, which are unique in their combination, distinguish the plant of the present invention from others of its class and permit its ready and sure identification, and are recited, by way of nonlimitative example, in the description which follows. In this description, plants are referred to which were cultivated in a greenhouse for about eight months in an exposed sunny spot on a hillside in Nice, France, the description applying to the condition of the plants in the month of March. There will of course be differences that arise by virtue of other climates or seasons or soil varieties or methods of culture, as are normally encountered under changed circumstances and as are well understood by persons having ordinary skill in this field; but these do not modify the important characteristics of the present invention as set forth below.

The color nomenclature in the following description is in accordance with the tables in the work "Horticultural Colour Chart" by Robert F. Wilson, which is hereinafter indicated by the initials HCC followed by the page number and the number of the shade of the color, except in those cases in which the color was not present in those tables or when the indication of color is sufficiently precise with reference to ordinary terminology.

Reference is also had to the accompanying drawings, which form a part hereof, and which show various portions of the plant and the condition of the plant budded and in bloom.

*Plant*

Overall Aspect.—Medium high to high, vigorous, dense, with moderately voluminous tufting, moderately thin, with moderately numerous floral branches, which are robust and are inserted at the base of the plant.

Average Height.—90 to 110 cm. from the ground for completely developed plants cultivated as indicated above.

Roots.—Of medium development, numerous, departing in tufts from the ground level, thin, little developed, about 100 to 150 mm. long and extending deep into the soil. Bearded root portions are not frequent and are of medium development, short and thin. Yellowish color.

Principal Stem.—Generally short, of medium thickness, subcylindrical, jointed between 2 to 4 internodes of segments of medium length. The nodes or joints have little to medium projection from the stem and are annular. The principal stem has mean dimensions which, as to their length, from the soil level to the first branch may be 20 to 50 mm. and a mean diameter at the soil level of 8 to 10 mm. The skin or peel of the principal stem is smooth or moderately rugose longitudinally, and is of green color tinged with hazel.

Flower Stems.—Moderately numerous, averaging six to eight in number, in different stages of development. In form, the flowering stems are robust and of moderate thickness, subcylindrical, of a mean diameter that varies from the base to the tip, somewhat fragile at the height of the joints and in segments that are moderately numerous. These stems are straight, slender, relatively rigid and bear the flower in an elegant and harmonious manner. The flower stems have mean dimensions such that the length from the base to the flower is 70 to 90 cm. and the mean diameter at the base is 4 to 7 mm.

The internodes or segments are moderately numerous to numerous, and average 14 to 16 on the flower stems. In form, they are quite variable according to the stage of development and the position on the stem. The basic internodes are subcylindrical, and a little enlarged near the joints, sometimes of elliptical section. The intermediate and higher internodes are quite elongated and thin and are enlarged like a club toward the lower joint, and are straight or a bit sinuous, with longitudinally extending clefts or flat places, sometimes canalized. The dimensions are variable according to their position on the stem. The length increases from the base toward the upper part of the stems, and then decreases in the internodes below the flower, according to the following typical schedule:

First internode from the base: 8–10 mm.; second: 10–12 mm.; third: 10–12 mm.; fourth: 10–12 mm.; fifth: 12–18 mm.; sixth: 25–30 mm.; seventh: 35–40 mm.; eighth: 45–50 mm.; ninth: 50–55 mm.; tenth: 60–70 mm.; eleventh: 80–90 mm.; twelfth: 90–100 mm.; thirteenth: 100–110 mm.; fourteenth: 100–110 mm.; fifteenth: 90–100 mm.; sixteenth: 60–65 mm. The floral peduncle is very short or practically sessile. The color is at the base Parsley Green (HCC, page 193, shade 00962) covered by areas of a thin waxy pellicle of the color Carnation Leaf Green (HHC, page 194, shade 0058/3). In texture, they are rigid, woody, and a bit flexible toward the end of the stem.

Joints.—Differentiated, rounded, moderately projecting from the stems, and a bit flattened on the sides of the leaves.

Leaves.—Abundant, inserted on all the joints in opposed pairs, interconnected at their bases in a foliate envelope which surrounds the joint and the base of the superposed segment, to a height of 8 to 10 mm., generally completely. In form, the leaves range from relatively long and moderately large, triangular, and acutely pointed at the base of the stems, to long and large, lanceolate, swordshaped, with a sharp point, farther up the stems. The lower leaves are concave, that is, centrally guttered or canalized while the middle and upper leaves are nearly flat or convex on their edges. The edges are smooth and are elevated little if at all above their central portions. The average dimensions of the leaves, are, as to their length, 150–170 mm. for lower leaves and 100–120 mm. for middle and upper leaves. The width of the lower leaves is 8–10 mm. and for the middle and upper leaves, 12–15 mm.

The color of the leaves is nearly Pear Green (HCC, page 197) shade 000858) covered with areas of a waxy coating of Carnation Leaf Green (HCC, page 194, shade 58/3). The surface of the leaves is smooth, glabrous, apaque or a bit pruinose. The leaf texture is thick, moderately fleshy and flexible in the lower leaves; and fleshy and rigid in the middle and upper leaves. The configuration of the leaves, for the lower leaves, is sinuous, frequently curved back on the base at an acute angle near the base, the middle and upper leaves diverge from the stems to a right angle or curve back toward the base in a simple arc, or unroll in a simple single or double spiral. The point of the leaf is directed downwardly.

Lateral Shoots.—More frequent at the base of the plant, with a tendency to bear flower stems, and more scarce in the middle and upper portions of the plant. The average length, midway of the height of the plant, is 150–170 mm. The configuration is less divergent than that of the stems.

*Flower*

Overall Aspect.—A single principal flower, erect, at right angles to the stem, often accompanied by a secondary floral bud carried by lateral shoots inserted at the upper joints of the stem.

Closed Flower Bud.—Large, ovoid, globular, with a moderately sharp point. The bud opens at this point. The average length to the opening of the sepals is 32–28 mm. and the diameter 20–25 mm.

Calyx.—Of the generally closed type but open during certain seasons along a single longitudinal line in a certain percentage of the flowers. The average dimensions are, with the corolla open: length 35–40 mm., diameter from the base to the points of the sepals, 25–28 mm. The sepals are five in number, are large, and are secured together in a conical tube for about three-quarters of their length and terminate in triangular irregular points that are scarious at their edges. The sepals are hump-backed at their base and curved over toward the outside at their edges.

The outer surface of the calyx is glossy, glabrous, opaque or a bit satiny. The interior is glossy, glabrous, waxy, glistening or satiny. In color, the outer face has a background color of Peapod Green (HCC, page 120, shades 61/1–2–3) which at the base of the sepals is shaded, toward the upper part, with Parsley Green (HCC, page 193, shades 00962–00962/1) with fine longitudinal streaks of the same color as the base. The inner face is Peapod Green (HCC, page 120, shades 61/1–2). In texture the calyx is of medium thickness, tough and leathery.

Calycle.—Formed by 4 to 6 bracts, ordinarily 4, arranged in opposed overlapping pairs, at the base of the calyx, to an average height of 14–16 mm. The points of the bracts are sharp, triangular and differentiated. The bracts have an average length of 13–15 mm. and an average width of 14–16 mm., while the interior bracts have an average length of 14–16 mm. and an average width of 18–20 mm.

Open Corolla.—Medium large, with a regular round contour or a bit elliptical, slightly rayed and festooned. The guard petals are undulant and longitudinally folded, horizontal and hang down a little over the calyx. The central petals are free, vertical, gathered, bent longitudinally or creased. The center of the flower is full, shallow, and a little detached from the exterior petals. The profile of the flower is fan-shaped when open and shallow above the calyx. The average diameter of the open fully developed flower is 80–100 mm. and its length from the base of the calyx to the tip of the petals is 50–55 mm.

The general color of the flower is basically Light Rose (HCC, page 126, shade 427/3) with marks shaded and mottled with Rose Clairet (HCC, page 109, shade 121/1).

The petals are numerous, averaging 60 to 70 in number, and are regularly inserted with several rudimentary petals at the center of the flower.

The guard petals have a large border or outer edge of rounded fan-shaped or heart shape, and are wider than they are long, are undulant and longitudinally folded, sometimes a bit corrugated on the sides, and often curved downwardly on the terminal edge. The base of the petal is long and wide, robust, with longitudinal veining. The outer edge of the border is fine-toothed, with short rounded teeth.

The interior petals have a border which is smaller and more irregular than the exterior or guard petals, in the form of a moderately open fan, almost spatulate, bent and creased on the outer edge, dentated with several notches. The teeth are very fine and short. The lateral edges are smooth and converge toward the base and are moderately long and wide with veining. The average dimensions of the exterior petals, for the outer edge, are a length 30–35 mm. and width 40–45 mm., and for the base, a length of 28–31 mm. and a width of 1–10 mm. For the interior petals, the edge has a length of 25–30 mm. and a widthof 25–28 mm. while the base has a length of 25–28 mm. and a width of 1–6 mm.

As to color, the upper surface of the petals has a background color of Light Rose (HCC, page 126, shade 427/3) with an area that is shaded and speckled at the center of the petal with Rose Clairet (HCC, page 109, shades 021/1–2). The lower face of the petal has the same colors as the upper face but these are less brilliant and more on the white side than the upper face. The marking at the center of the petal is less pronounced.

The surface of the petals, on the upper face, is velvety, and satiny on the lower face. The texture of the petals is moderately thick to thick and strong.

Reproductive Organs.—The stamens are generally not numerous, averaging six to ten about the ovary, in the transformed portion and are partly in the form of petaloids. The threadlike parts which support the anther of the stamen are erect, thin, white and of a length of about 18–20 mm. The anthers are generally absent although sometimes present and fertile, but small. The ovary is of the color Light Green, raised, pear shaped and moderately ribbed. The styles, that is, the parts of the pistil that bear the stigma, are generally two in number, short, tubular, curved inwardly and crossed, white at the top and a bit tinted with red at the point. The stigmata are present on the inner side of the styles.

Odor.—Sweet carnation odor, weak to moderate in strength.

Resistance of Flowers to Climate.—Very good.

Resistance of Flowers to Packaging and Shipment.—Very good.

Durability of Cut Flowers.—Very good.

Resistance of the Plant to Disease.—Very good.

Flowering.—Abundant and continuous.

Having described my invention, I claim:

1. The new and distinct variety of carnation plant as described and illustrated.

No references cited.

ROBERT E. BAGWILL, Primary Examiner